United States Patent [19]

Steinemann

[11] 4,219,015
[45] Aug. 26, 1980

[54] PLATES FOR OSTEOSYNTHESIS
[75] Inventor: Samuel Steinemann, St. Sulpice, Switzerland
[73] Assignee: Institut Straumann AG, Switzerland
[21] Appl. No.: 897,370
[22] Filed: Apr. 18, 1978
[30] Foreign Application Priority Data
Apr. 22, 1977 [CH] Switzerland ............... 5011/77
[51] Int. Cl.² ..................... A61F 5/04; A61B 17/18
[52] U.S. Cl. ..................................... 128/92 D
[58] Field of Search ............ 128/92 D, 92 R, 92 BA, 128/92 BB, 92 G

[56] References Cited
U.S. PATENT DOCUMENTS

| 1,105,105 | 7/1914 | Sherman | 128/92 D |
| 3,463,148 | 8/1969 | Treace | 128/92 D |
| 3,528,085 | 9/1970 | Reynolds, Jr. | 128/92 D |
| 3,552,389 | 1/1971 | Allgower et al. | 128/92 D |

FOREIGN PATENT DOCUMENTS 742618  1/1933  France ................... 128/92 D

OTHER PUBLICATIONS

MOT, 6/74, pp. 168-174, (article by Von V. Goymann).
Hicks Anti-Rotation Lugged Plates (Stainless Steel, Titanium), Orthopaedic Catalogue, Down Bros. and Mayer & Phelps, Ltd., p. G55, 1966.
The Richards-Hirschhorn Compression Bone Plating System, (advertisement), The Journal of Bone & Joint Surgery, British vol. 53-B, No. 3, Aug. 1971 (4 pages).
Bone Plates Sherman-Type Plates, Cat. No. 6321, Vitallium Surgical Appliances (book), Austenal Laboratories, Inc., New York, N.Y., p. 7, Mar. 1948.

Primary Examiner—Ronald L. Frinks
Attorney, Agent, or Firm—McGlew and Tuttle

[57] ABSTRACT

The invention relates to an elongate plate for osteosynthesis. The plate comprises at least two screw holes and a respective hole-free longitudinal section separating each neighboring pair of the screw holes. A spacing, perpendicular to the longitudinal direction of the plate, between two mutually opposite surfaces of at least two sections containing the screw holes is greater than that between two mutually opposite surfaces of the hole-free sections. The plate exhibits at least in the region of the screw holes a bending resistance amount $W=I/e$ along a plane extending substantially centrally of the plate in the longitudinal direction of the plate and intersecting substantially perpendicularly that surface of the plate which is intended to rest on a bone. The bending resistance moment $W=I/e$ lies between a lower and an upper limiting value, the lower limiting value being at most 30% smaller than the upper limiting value, wherein I is the polar moment of inertia, and e is the maximum value of the distance of the outline bounding the cross-sectional area from a neutral surface of the plate.

15 Claims, 13 Drawing Figures

PLATES FOR OSTEOSYNTHESIS

BACKGROUND OF THE INVENTION

By the term "osteosynthesis", one understands fixation of bone parts by means of inserted implants taking place after a bone fracture. In this connection, reference is made to, for example, the book "Manual der Osteosynthesis" by M. E. Muller, M. Allgöwer and H. Willenegger, which was published by Springer-Verlag in 1969. Various types of osteosynthesis plates are described there and it is also explained how these have to be screwed fast to the parts of a broken bone. The bearing surfaces, by which the plates rest on the bone, can be flat or slightly curved. The screw holes are formed either by drilled holes or by slots. The so-called dynamic compression plates are of great importance. In these, at least one of the screw holes is formed by a slot, which extends in the longitudinal direction of the plate and which is inclined at the one end. When a screw is inserted at the inclined end of the slot, it causes a displacement of the plate in its longitudinal direction. It can thereby be attained that the bone parts at the location of the fracture are firmly pressed against each other. Such compression plates and their uses are, apart from the already mentioned book, described in the book "Die dynamische Kompressionsplatte DCP" by M. Allgöwer, L. Kinzl, P. Matter, S. M. Perren and T. Rüedi, published by Springer-Verlag in 1973, as well as in the publication "A dynamic compression plate" by S. M. Perren, M. Russenberger, S. Steinemann, M.E. Muller and M. Allgöwer; Acta Orthop, Scand. Suppl. 125, 29, 1969. The constructions in Swiss Pat. No. 462,375 and the corresponding U.S. Pat. No. 3,552,389 are the basis of the dynamic compression plates described particularly in these documents. With known plates displaying only round holes, the compression and re-positioning of the fracture zone is attained by means of a special tension device which is anchored to the bone and then engages the bone plate screwed in a preceding step to the other bone fragment.

These previously known plates of metal usually have the same crosssectional dimensions along their entire length and are thus formed by a profile rod. These plates have, in general, well stood the test. When the broken bone, the parts of which are held together by the plate, because of any kind of peculiarity does not unite together or when the plate is not correctly fastened during the operation, it can happen in exceptional cases that the plates break. These cases account for some 0.5 to 2% of osteosynthesis fracture treatments. The breakage point of the plates in this case always lies at one of the screwholes, since the cross-section of the plate, i.e. the strength, is reduced at these locations.

From U.S. Pat. No. 3,463,148, there is already known a plate in which the height, i.e. the cross-sectional dimension parallel to the passage direction of the screw holes, is greater in the region of the screw holes than in the regions between them. The variation of the height of the plate is so arranged that the material of the plate displays a substantially constant cross-sectional area over the entire length of the plate. This constant cross-sectional area should result in a substantially constant strength over its entire length.

The cross-sectional area determines the strength of the plate in tensile stress. When the height of the plate is now so increased at the screw holes that the cross-sectional area of the material remains constant, the plate indeed receives a constant tensile strength over the entire length. However, an unnecessary increase in the bending stiffness results at the screw holes. As will still be explained later, the tensile strength is on the one hand however only of secondary importance to fatigue fracture strength, while the bending stiffness on the other hand may not be varied arbitrarily.

For the rest, the previously known concept results in various disadvantages depending upon the remaining demands on the plate. The crosssectional dimensions of the plate must naturally be adapted to the dimensions of the bones. For fractures of the tibia (the shin bone), compression plates are now for example used, the width of which amounts to about 11 millimeters. The width of a slot of such a compression plate then varies between 5.5 and 8 millimeters. For such a compression plate, the width of the slots is thus relatively great in relation to the width of the plate. When, in the case of such a compression plate, it is desired to make the cross-sectional areas constant over the entire length of the plate, the height of the plate at the slots must be about 50 to 60% greater than in the remaining regions. If such a pressure plate were inserted in a bone, a considerable danger would exist that the tissue, and in particular the skin, disposed on the side of the plate remote from the bone would be damaged. A further disadvantage of this plate is that its bending stiffness to bends along a plane running parallel to the longitudinal direction of the plate and to the passage direction of the slots is considerably increased. The bending stiffness of a plate should however lie within a predetermined range for each bone. When the bending stiffness is namely too small, a bone-resorption, i.e. a dissolution of the bone, can take place in the fracture gap because of too vigorous movements of the bone parts. When the bending resistance is, on the contrary, too great, the bone is insufficiently loaded, which has the consequence of an osteoporosity, i.e. a decalcifying and weakening of the entire bone.

Previously also known in this field is a plate, namely the plate according to Sherman, the width of which measured perpendicularly to the passage direction of the screw holes is greater in the region of the screw holes formed by countersunk holes then in the remaining regions. This known plate is about 7 millimeters wide between the screw holes and about 10 millimeteres wide at the screw holes. The screw holes display a cylindrical section of 4 millimeters in diameter and a conical countersinking, the maximum diameter of which amounts to about 6.5 millimeters. A considerable danger of breakage in the region of the screw holes likewise exists in the case of this plate. Moreover, this plate is over 40% wider at the screw holes than between these. Such relatively large projections however result in a great danger of injury to the soft body tissues and the skin in the neighborhood of the plate with the movements of the patient.

According to the operational technique at present taught and applied in surgery, the plates should be inserted in such a manner that they are loaded exclusively in tension. When this is the case, fractures hardly occur in the plates of constant cross-sectional dimensions over their entire length as described in the two books already mentioned, the Swiss Pat. No. 462,375 and the U.S. Pat. No. 3,552,389. As already mentioned, the plates can however break in extreme cases. Such cases possibly arise with complicated fractures, porous bones, delayed healing or when the patient displays an extremely great body-weight or is excessively active motionally. It has now been recognised that breakage of the plate were caused not by single peak loadings, but were a consequence of the material fatigue because of repeated, relatively great loadings. It has been further ascertained through the evaluation of clinical experience that the plate breakages were caused not by tensional stresses, but by bending stresses or eventually torsion. Decisive in that case are those bending stresses which occur when the plate is bent along a plane which extends parallel to the longitudinal direction of the plate and at least approximately parallel to the opening of the screw holes, i.e. the screw axes and, indeed, above all, in the case of those bendings in which the plates at its surface remote from the bone, is stressed in tension.

SUMMARY OF THE INVENTION

According to the invention there is provided an elongate plate for osteosynthesis, comprising at least two means each defining a respective hole for receiving a screw, and a respective hole-free section extending in the longitudinal direction of the plate and separating each neighboring pair of the means defining the holes, a spacing, perpendicular to the longitudinal direction of the plate, between two mutually opposite surfaces of at least two of said hole-defining means being greater than that between two mutually opposite surfaces of the hole-free sections, the plate exhibiting at least in the region of the at least two hole-defining means a bending resistance moment $W = I/s$ along a plane extending substantially centrally of the plate in the longitudinal direction of the plate and intersecting substantially perpendicularly that surface of the plate which is intended to rest on a bone the bending resistance moment $W = I/e$ lying between a lower and an upper limiting value, the lower limiting value being at most 30% smaller than the upper limiting value, wherein I is the area moment of inertia, and e is the maximum value of the distance of the outline bounding the cross-sectional area from a neutral surface of the plate.

A plate embodying the invention is strengthened in such a manner that in problem cases of the operative treatment of bone fractures as well as for orthopaedic operations (correction of bone-displacement among others), plate breakages may no longer occur. To this end, as will be explained hereinafter, it does not suffice to dimension the plates more strongly, since certain prerequisites or secondary considerations ought to be fulfilled. These considerations are given by biomechanical conditions and the operational technique. These are:

(1) The bone plate should, preferably, have a favorable bending resistance matched to the bone to be fixed. If the plate is very flexible, then the region of the fracture is not sufficiently stabilized and bone resorption in the fracture gap results due to movement. On the other hand, if the plate is very stiff, then the plate takes up all loading forces. The functional loading of the bone is then absent and this may lead to general decay of the bone (porosity). In between lies an optimum stiffness. This stiffness is a function of the shape of the plate and of the specific elasticity of the material.

(2) The bone plate should, preferably, have as small a volume as possible so that the displacement of the surrounding tissue due to the normal body defense reactions remains small. This consideration should also result in an economy of metal.

(3) The exact repositioning of the bone fragment requires, for the operational treatment of the fracture, that the plates are adapted to the shape of the bone. One uses forceps and presses during the operation for this adaptation. The previously known plates formed by profile rods, frequently kink in the region of the screw holes while being adapted to the shape of the bone, since they are at their weakest there. Thereagainst, those previously known plates, in which the cross-sectional area of the plate material is constant over the entire length, frequently kink between the screw holes while being adapted to the shape of the bone. In both cases, kinds thus arise in the shaping to be performed before the fastening of the plate and not the desired steady curvature.

First, some possible cross-sectional shapes of the plate as well as some geometrical concepts shall be explained. The plates can be rectangular in cross-sections, in which case one of the two wider longitudinal surfaces then forms the bearing surface intended to rest on the bone. The plates can however deviate to a greater or lesser extent from this basic shape in various ways. It is first to be mentioned that the bearing surface, by which the plate is intended to rest on the bone, need not be flat, but may be formed by the section of a cylindrical surface, wherein the cylinder axis is parallel to the longitudinal direction of the plate. The radius of curvature should then of course correspond approximately to the radius of the bone concerned. The plate could however at the longitudinal edges of the bearing surface display also two longitudinal ribs projecting against the bone. The middle section of the bearing surface disposed between the longitudinal ribs could then be planar, while all transitions would be rounded.

The plates can be symmetrical with respect to the longitudinal center plane over their entire length. In this case, which is explained in detail hereinafter with reference to two specific embodiments, the screw holes are of course also symmetrical with respect to this longitudinal center plane and the axes of the screws lie in the longitudinal center plane during the assembly. As will likewise be explained with reference to the specific embodiments, the screw holes can also be laterally displaced relative to the longitudinal center plane. In this case, it is only in the longitudinal sections located between the screw holes, that the plate is symmetrical with respect to the longitudinal center plane which cuts perpendicularly the surface intended to rest on the bone. For the rest, the passage directions of the screw holes of the plate, in that case, do not all need absolutely any longer to be exactly parallel to one another.

The plate is bounded by four longitudinal surfaces which lie opposite one another in pairs. If one takes a cross-section through the plate at any location, the longitudinal surfaces lying opposite one another can yield lines of intersection which are parallel to one another, but need not be. The spacing of the opposite lines of intersection can thus be different at different locations of the cross-section. For the remainder, the spacings can vary also in the longitudinal direction of the plate. In the following, by the term width is to be understood the maximum spacing of the two opposite longitudinal surfaces laterally bounding the plate measured in an arbitrarily chosen cross-section perpendicular to the longitudinal center plane. Furthermore, by the term height is to be understood the maximum spacing between the bearing surface intended to rest on the bone and the opposite longitudinal surface measured in an arbitrarily chosen cross-section perpendicular to the longitudinal direction of the plate and parallel to the longitudinal center plane. The width and the height are thus two cross-sectional dimensions which can vary in the longitudinal direction of the plate. At least one of these two cross-sectional dimensions must now be greater at the screw holes than in the longitudinal sections between the screw holes.

The plates display preferably more than two screw holes, namely at least four and, for example, six screw holes. With the use of a plate displaying at least four screw holes, in general, smaller bending stresses occur at the two screw holes disposed at opposite ends of the plate than at the inner, i.e. the central, screw holes disposed in the vicinity of the point of fracture of the bone, If the plate displays four or more screw holes, it is therefore, in some circumstances, permissible that the plate is strengthened only at the screw holes disposed in its middle part. The bending resistance moment can be smaller at the two screw holes disposed at the opposite ends of the plate than at the remaining inner screw holes and in the longitudinal sections between these. Preferably, the resistance moment at all the screw holes is however at least approximately the same as in the longitudinal sections between the screw holes. The plate is however preferably rounded at its ends, i.e. beyond the two outermost screw holes, and accordingly there displays a smaller resistance moment than in the remaining regions. In the following, the bending resistance moment is also then designated as approximately constant over the entire length of the plate, when it is smaller immediately at the ends of the plate, i.e. beyond the outermost screw holes, than at the screw holes and between these.

In a plate embodying the invention, the bending resistance moment is thus within the stated tolerance limit at least at the inner screw holes and thus nearly constant over the principally stressed longitudinal region of the plate. In an expedient development of the plate, the lower limit value of the resistance moment is at the most 15% smaller than the upper limit value. Thereby, the plate receives a nearly constant strength against breakage in the whole of its portion stressed in bending. Furthermore, such a plate lets itself be adapted to the shape of the bone without kinks occurring at certain places.

The local strengthening of the plate in the region of the screw holes permits the mean bending stiffness of the plate to be adjusted to an optimum value. Since the bending stiffness increases more markedly with an increase in the height of the plate than the resistance moment, namely by the third power of the height in a plate with rectangular cross-section, it is advantageous to make the resistance moment at the screw holes as closely as possible exactly the same as between them. The constancy of the resistance moment is of course limited by the manufacturing tolerances. Furthermore, small deviations result in an expedient shaping because no sharp edges and corners shall occur. At these, so-called stress concentrations would namely arise and promote the occurrence of fissures. The plate should therefore be so manufactured that its contours everywhere vary smoothly. The radii of curvature can however be so chosen that the regions, in which the resistance moment deviates from the predetermined nominal value due to the necessary roundings, display a length which amounts to less than 10% of the width of the plate. For the rest, the deviations of the resistance moment from the nominal value caused by manufacturing tolerances and the roundings can be limited to a few percent so that the resistance moment over the whole length of the plate lies within the limit values mentioned hereinbefore.

Tissue reactions of the body against implants of foreign body material generally increase with increasing volume of the implant. It is therefore expedient to keep the volume of the plate as small as possible. Since, for the achievement of a constant resistance moment, the cross-sectional area of the plate at the screw holes now needs to be enlarged less when one increases only the plate height than when one increases only the plate width, the plate height is advantageously made greater at the screw hole regions than in the remaining regions.

Preferably, the height of the plates is always greater at the screw holes than in the longitudinal sections disposed between these. At least in plates, for which the plate width between the screw holes is relatively small in comparison with the width of the latter, expediently, not only the width or only the height of the plate is increased at the screw holes, but the width as well as also the height. Thereby, an at least nearly constant resistance moment can be attained without extreme increases of the width or height being necessary in the regions of the screw holes. The width of the plate should be at the most 20% larger in the region of the screw holes than in the remaining regions.

BRIEF DESCRIPTION OF THE DRAWINGS

Embodiments of the present invention will now be more particularly described by way of example with reference to the accompanying drawings, in which.

DESCRIPTION OF THE PREFERRED EMBODIMENTS

Figures 1, 2, 3, 4, 5, 6, 7:
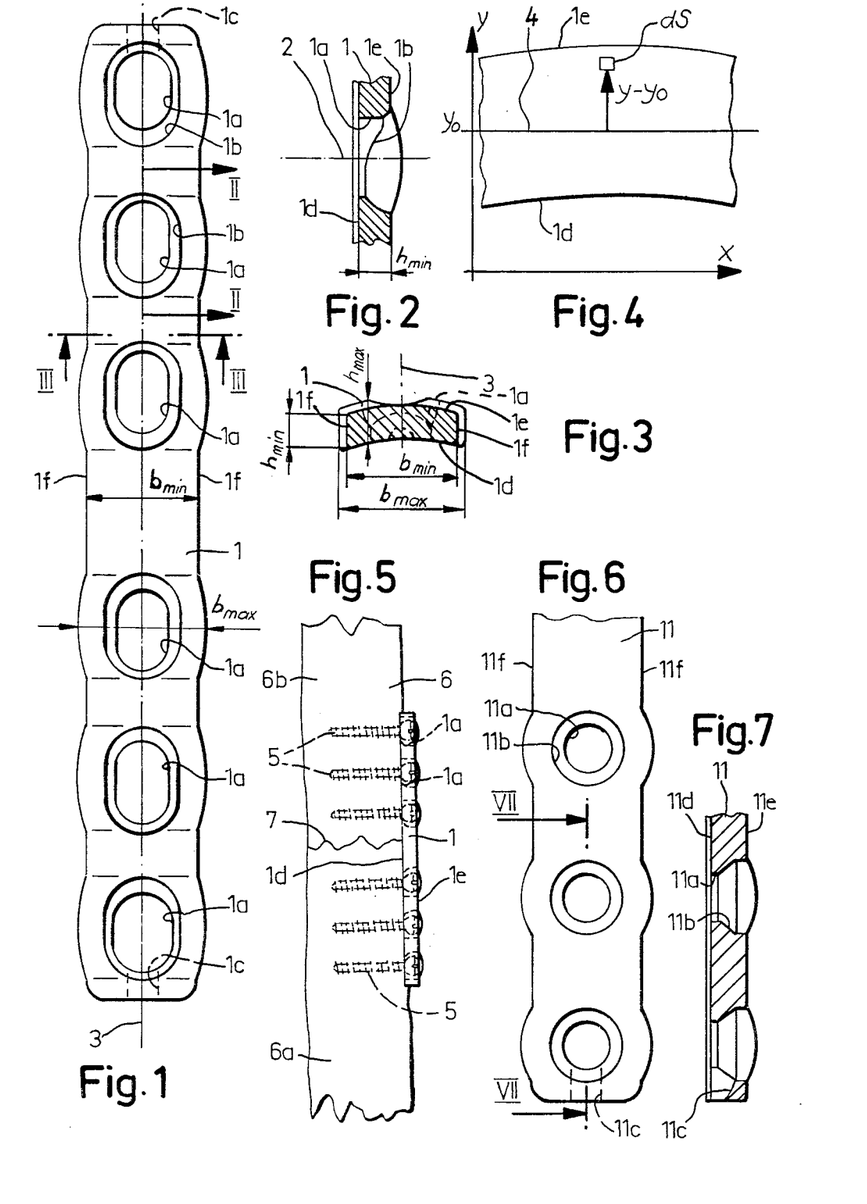
FIG. 1 shows a plan view of a plate embodying the invention for tibia fractures.
FIG. 2 shows a section along the line II—II of the FIG. 1.
FIG. 3 shows a section along the line III—III of the FIG. 1.
FIG. 4 shows a diagram to illustrate the calculation of the moments of inertia and resistance.
FIG. 5 shows an elevation of a broken tibia, the fragments of which are connected to each other by a plate embodying the invention.
FIG. 6 shows a plate with round screw holes and embodying the invention.
FIG. 7 shows a section along the line VII—VII of the FIG. 6.

Referring now to the drawings, FIGS. 1, 2 and 3 show an elongate metal compression plate 1 for the osteosynthesis of fragments of the tibia (the shin-bone) and other bones, possibly the upper arm bone. The compression plate 1 is provided with several, namely six, screw holes 1a distributed over its length. The spacing between the two central screw holes 1a is greater than that between the other adjacent screw holes 1a. The screw holes are developed as slots running in the longitudinal direction of the plate and display a countersink 1b on a wide side of the plate. The direction of penetration of the screw holes 1a, i.e. the direction in which the screw axes run during the screwing fast of the plate 1, is indicated by 2. The screw holes 1a are symmetrical with respect to the longitudinal center plane 3 running parallel to the directions of penetration 2 in the longitudinal direction of the plate 1. As is apparent from FIG. 2, the countersinks 1b are however asymmetrical in longitudinal section. Each countersink is inclined from that end of the slot, which faces the nearer end of plate 1, to about the middle of the slot. At the end of the slot, which is disposed on the side of the more distant end of the plate, the countersink is steeper and forms a portion of a spherical surface. Reference is made to Swiss Pat. No. 462 375 and to U.S. Pat. No. 3,552,389 corresponding thereto, in which the development of the screw holes of compression plates is extensively described. A longitudinal groove 1c, which extends up to the penetrating opening of the slot, is milled in the side facing away from the countersink 1b at each end of the plate 1.

The compression plate is approximately rectangular in cross-section. As is evident from FIG. 3, the two longer sides of the rectangle are however formed by circular arcs running parallel to each other. The longitudinal surface 1d, intended to rest on a bone, of the plate 1 cuts the longitudinal center plane 3 at right angles and forms a concavely curved cylindrical surface over its entire length. The longitudinal surface 1e lying opposite the longitudinal surface 1d is convexly curved and, in the longitudinal section between the screw holes 1a, cylindrical and coaxial with the surface 1d. Thereagainst, it displays convex bulges at the screw holes 1a, or stated more exactly, at the countersinks 1b. The other two narrower longitudinal surfaces 1f run parallel to the passage directions 2, and outside the regions of the screw holes 1a, parallel to one another and to the plane 3. They are laterally curved outwards at the screw holes 1a.

By the heigth h of the compression plate 1 is to be understood, for each cross-section through the plate 1, the maximum cross-sectional dimension measured at right angles to the longitudinal direction of the plate and parallel to the longitudinal center plate 3, i.e. the maximum spacing of the two mutually opposite longitudinal surfaces 1d and 1e measured parallel to the passage direction 2 of the screw holes. By the width b is to be understood, for each cross-section of the plate, the maximum cross-section dimension measured at right angles to the longitudinal centre plane 3 of the plate and thus also to the passage direction 2 of the screw holes, i.e. the spacing of the two mutually opposite longitudinal surfaces 1f. In the longitudinal regions of the compression plate 1 disposed between adjacent screw holes 1a, the height h and the width b are constant and have the values $h_{min}$ and $b_{min}$, respectively. In the longitudinal regions of the plate containing the screw holes, the height h as well as also the width b are greater than in the hole-free longitudinal regions. The maximum values of the height and width are designated by $h_{max}$ and $b_{max}$, respectively. In that case, the width b varies over the longitudinal direction of the plate in such a manner that the plate is symmetrical with respect to the plane 3.

Before it is explained how the height h and the width b vary along the plate, a few concepts of the theory of bending of elastically deformable bodies must first be explained with reference to FIG. 4. FIG. 4 shows a portion of a cross-section of the plate. Since in FIG. 4, a diagram for the illustration of a few physical quantities is concerned, no hatching was applied. In use, the plate, as will be hereinafter described with reference to FIG. 5, is so fixed that the surface 1d rests on the bone 6 and the surface 1e is remote from the bone. It is assumed that the plate is curved along the longitudinal center plane 3. The bending can possibly take place so that the surface 1d becomes concavely curved in the longitudinal direction of the plate 1. It is further assumed that the plate 1 is not acted upon during the bending by any external force running in its longitudinal direction and that also no torsion occurs. In the elastic deformation, one is only concerned with pure bending. Within the plate 1, there then results a neutral axis running in the plane 3 and a neutral surface, in which the plate material is neither stretched nor compressed during the bending. Thereagainst, the plate material disposed between the neutral surface and the surface 1e is stretched and the plate material disposed between the neutral layer and the surface 1d is compressed. A Cartesian co-ordinate system in the plane of the cross-sectional is applied in such a manner that the x-axis runs at right angles to the plane 3, along which the plate 1 is curved. The y-axis runs parallel to the plane 3 along which the plate 1 is bent. The y-axis is counted positive in that direction which is remote from the bone and, thus, runs from the surface 1d to surface 1e. The z-axis, not visible in the FIG. 4, runs parallel to the longitudinal direction of the rod. For small bands, the neutral surface runs through a straight line 4 parallel to the x-axis at the co-ordinate $y_o$. This is determined by the following formula:

$$y_o = \int y\, dA / \int dA \qquad (1)$$

In this case, dA designates an element of area of the cross-sectional area. The integral is to extend over the whole area of the cross-section. As is evident from equation (1), the neutral surface extends through the center of gravity of the cross-sectional area.

An area moment of inertia is now defined with respect to the straight line 4 parallel to the x-axis. The area moment of inertia I is given by the equation $$I = \int (y - y_o)^2 \cdot dA \qquad (2)$$

The integration is in that case again to extend over the entire crosssectional area. In the region of the screw holes, the integrals of the equations (1) and (2) are of course only to extend over the material of the plate i.e. the screw holes are to be excepted from the integration. Furthermore, one defines a bending resistance moment W which is given by the equation $$W = I/e \qquad (3)$$

In that case, e designates the maximum value of the spacing of the outline bounding the cross-sectional area from the neutral surface, i.e. the straight line 4. Expressed as an equation, this gives $$e = \max |y - y_o| \qquad (4)$$

The values $W_1$ and $W_2$ defined by the following equations are likewise designated as resistance moments:

$$W_1 = I/e_1 \qquad (3a)$$

$$W_2 = I/e_2 \qquad (3b)$$

wherein $e_1$ is the maximum distance of the outline bounding the crosssectional area from the neutral surface 4 on the side remote from the bone. Likewise, $e_2$ is the maximum value of the distance of the outline bounding the cross-sectional area from the neutral surface on the side resting on the bone. This can be expressed by the equations:

$$e_1 = \max(y - y_o) \qquad (4a)$$

$$e_2 = \max(y_o - y) \qquad (4b)$$

In the case where the plate in cross-section were to display an exactly rectangular outline with the width b and the height h, then $e = e_1 = e_2 = h/2$ and for the moments, I, W, $W_1$ and $W_2$ the following values would be obtained:

$$I = b\,h^3/12 \qquad (2a)$$

$$W = W_1 = W_2 = I/(h/2) = b\,h^2/6 \qquad (3c)$$

In a plate with a rectangular cross-section, e, $e_1$ and $e_2$ and W, $W_1$ and $W_2$ would be of equal value respectively. This is however in general and especially in the case of the plates shown in FIGS. 1 to 3 not the case.

Since the screw holes 1a have complicated outline shapes in crosssection, a calculation of the integral equation in the region of the screw holes is not possible or at least very difficult. When the outlines are given, one can however determine the integrals (1) and (2) graphically or numerically according to known methods.

The cross-sectional dimensions and shapes are now varied along the plate in such a manner that the resistance moments W, $W_1$ and $W_2$ substantially remain nearly constant over the entire length of the plate 1, i.e. at every location in the longitudinal regions containing the screw holes and in the longitudinal regions disposed between the screw holes. By nearly constant is meant in this case that the resistance moment lies between an upper and a lower limit value and that the lower limit shall be at the most 30% smaller than the upper limit. The lower limit value is preferably at the most 15% smaller than the upper limit value. Likewise, each of the resistance moments $W_1$ and $W_2$ also lies between the two limit values, of which the lower limit is at most 15% smaller than the upper limit.

As given in equations (3), (3a), (3b) and (4), (4a), (4b), W is equal to the lower of the two values $W_1$ and $W_2$. In the described plate, $W_1$ at most of the plate positions is approximately as large as $W_2$ or somewhat smaller than $W_2$, whereby the difference amounts to at most about 15%. The values W and $W_1$ are, therefore, identical at most of the plate positions. The resistance moment W should amount to at least 15 cubic millimeters, for example 20 to 25 cubic millimeters. At the two outermost end sections of the plate 1, i.e. between the outermost screw holes and the ends of the plate, where the plate 1 is stressed only a little and is rounded in accordance with FIG. 1, the resistance moments may theragainst readily be somewhat smaller. One could even dispense with the enlargement of the cross-sectional dimensions at the two outermost screw holes themselves.

Expediently, the surfaces 1d, 1e and 1f are of such a nature that no sharp edges result at the transition locations where the cross-sectional dimensions alter. Or, said in other words, the transition locations shall be rounded. Thereby, it is prevented that the stress concentrations occur at the transition locations during the stressing of the plate 1. The roundings at the transition location can however readily display such small radii of curvature that the resistance moment lies between the above-defined limit values even at the transition locations.

In the use of the plate 1, it is subjected to a bending moment that at a maximum is to have the value M. The maximum stress $\sigma$ existing in the plate is then $$\sigma = M/W \qquad (5)$$

If the value $W_1$ is substituted for the value W in equation (5), there results, in the plate region between the neutral surface and the surface 1e remote from the bone, the maximum tension. If, instead, the value W were replaced by $W_2$, there results, by analogy, the maximum value of the tension, which appears in the region between the neutral surface and the surface 1d resting on the bone.

Furthermore, $\delta_D$ is to designate the fatigue breaking strength on repeated bending stress of the material of the plate, i.e. that maximum tensile stress occurring in a bending-oscillation test at which the plate in a repeated oscillation test just fails to break for a given large number of loading cycles. The fatigue breaking strength with repeated bending stress can readily be ascertained experimentally, wherein the number of loading cycles can for example, amount to one million or more.

One can solve equation (5) for the bending moment M, insert the value $\delta_D$ for the stress as well as the smallest value of the resistance moment W and then obtain the maximum permissible bending moment, at which the plate still does not break with continued alternating loading. If one proceeds from a plate which displays constant cross-sectional dimensions over its entire length and now strengthens the plate at the screw holes in accordance with the invention, then the permissible bending moment is considerably increased.

As already mentioned in the introduction, apart from the breaking strength, the bending stiffness is also a very important biomechanical magnitude. The bending stiffness is equal to the product: E.I, where E designates the modulus of elasticity of the plate material. The compression plate intended particularly for the osteosynthesis of the tibia has a width of about 10 to 14 millimeters, for example 12 millimeters in the longitudinal hole-free region. The clear width of the screw holes, i.e. the width of the slot, amounts to at least 5 millimeters, namely about 5.5 millimeters. The countersinks have a width of approximately 8 millimeters at their widest location. The height h of the plate 1 and the modulus of elasticity of the plate material are now matched to each other in such a manner that the mean value S of the bending stiffness E.I. averaged over the entire length of the plate amounts to $3 \cdot 10^5$ to $7 \cdot 10^5$ kilopond-square-millimeters. When the mean bending stiffness S lies in the range of magnitude, an optimum healing takes place with fractures of the tibia so that, in particular, neither a bone resorption nor an osteo-porosis takes place. The modulus of elasticity E is constant in the entire plate. The mean bending stiffness is thus given by the expression:

$$S = \overline{EI} = \frac{E}{l} \int_0^l I(z)\, dz \tag{6}$$

In this case, $\overline{I}$ designates the mean value of $I(z)$, $l$ the length of the plate, $z$ the length co-ordinate and $dz$ an element of length. The mean value of the area moment of inertia $\overline{I}$ can be approximately determined numerically by subdividing the plate into finite length intervals, calculating the area moment of inertia for each interval and then replacing the integration of equation (6) by a summation. Since the cross-sectional shape changes relatively quickly in the longitudinal direction of the plate in the region of the screw holes, one should in order to obtain a good accuracy subdivide the longitudinal section of the plate containing a screw hole into at least ten intervals of length for the numerical calculation of the integral. Such narrow intervals are of course also necessary for the calculation of the resistance moment.

The mean bending stiffness can also be determined experimentally on the completed plate in that one for example lets a certain bending moment be applied to the plate so that the plate is elastically bent and measures the mean radius of curvature. The bending resistance is namely equal to the product of radius of curvature times bending moment and thus can be calculated from the mean radius of curvature and the given bending moment. One can of course determine the deflection and curvature of the plate also by a so-called four-point application of the forces, in which forces act upon the plate at four locations, namely upwardly directed forces at the two inner locations and downwardly directed forces at the two outer locations.

The cross-sectional dimensions of the plate 1 can be so fixed that the mean area moment of inertia $\overline{I}$ amounts to 25 to 70 millimeters$^4$. For the favourable shape correction, particularly the ratios between the resistance moment and the mean area moement of inertia, namely $W\sqrt{\overline{I}}$, $W_1\sqrt{\overline{I}}$, $W_2\sqrt{\overline{I}}$, are important, and these should amount to at least 0.3 per millimeter, better still to about 0.4 per millimeter, at the screw holes as well as at the longitudinal sections between these. The metal used for the plate must of course have a great resistance to corrosion and be compatible with the body tissues. Practical metals have quite different properties affecting the bending strength and bending stiffness. With different metals it is expedient to increase the strength by cold working. If the plates are manufactured from sectional rods, material must be removed at the outer surfaces at least here and there so that the outline of the plate cross-section alters along the plates longitudinal direction in the described manner. In the above-mentioned cold worked metals, material can be removed, for example, by an electromechanical process. It is self-evident that the material can also be removed by milling or cutting, whereby profile gauges may be used.

There are, however, metallic materials, which for the attainment of sufficient strength certainly must not be cold-worked but can be forged when hot, whereby the forging temperature continuously determines the strength properties. With these metallic materials the external shape of the plates can be produced during forging and, eventually, also the holes can be produced through forging.

The plates can, for example, comprise cold-worked stainless steel which contains 17 to 20% chromium, 10 to 15% nickel and 2 to 4% molybdenum, balance substantially all iron. Suitable materials for manufacture of plates which do not necessarily undergo cold working but are forged when hot, are titanium, titanium alloy with at least 75% titanium and high-strength cobalt alloy with at least 20 to 70% cobalt. As a cobalt alloy, a known alloy designated syntacoben can be used. This alloy has the following composition: 18–22% chromium (Cr), 5–15% iron (Fe), 15–25% nickel (Ni), total of 6–8% molybdenum plus tungsten (Mo+W), 0.5 to 2.5% titanium (Ti), max. 1% manganese (Mn), max. 0.5% silicon (Si), max. 0.05% carbon (C), max. 0.01% sulphur (S), remainder cobalt. An example of a titanium alloy is the alpha-beta alloy Ti 6 Al 4 V. In the following table the modulus of elasticity E, the fatigue breaking strength with repeated bending stress $\sigma_D$ and the likewise still more important value $\sigma_D/E^{\frac{2}{3}}$ are given for four of the above-mentioned materials.

| Raw material | E kp/mm$^2$ | $\sigma_D$ kp/mm$^2$ | $\sigma_D/E^{\frac{2}{3}}$ kp$^{\frac{1}{3}}$/mm$^{\frac{2}{3}}$ |
|---|---|---|---|
| cold-worked stainless steel | 19000 | 40 | 0.06 |
| titanium | 10600 | 35 | 0.08 |
| SYNTACOBEN | 22000 | 70 | 0.09 |
| Ti 6Al 4V | 11600 | 45 | 0.09 |

When the mean bending stiffness shall, for biomechanical reasons for example, amount to $S = 6\cdot10^5$ kp·mm$^2$, the mean polar moment of inertia $\overline{I}$ must be about 32 mm$^4$ for stainless steel and around 57 mm$^4$ for titanium. When the width of the plate is given, then the heights are to be adapted correspondingly. Since the mean polar moment of inertia $\overline{I}$ is decisive for the mean bending stiffness S, the local polar moment of inertia $I$ becomes less in the longitudinal sections disposed between the screw holes and greater in the hole regions than the mean value $\overline{I}$. Mean polar moments of inertia of the stated magnitude let themselves be realized when the plate has a width of about 10 to 14 millimeters and a height of about 3 to 4.5 millimeters in the hole-free regions. A resistance moment nearly constant over the entire length of the plate lets itself be obtained for example when the height h in the hole centers is made about 30 to 40%, and the width b 10 to 20%, namely about 15%, greater than in the hole-free regions. In order that the widenings of the plate 1, when this is fastened to the bone of a patient, should not by his movements damage the skin and other soft tissue parts disposed in the vicinity of the plate, the width b in the region of the screw holes shall be at most 20% greater than in the longitudinal regions between the screw holes. The height h should preferably be at most 50% greater at the screw holes than in the hole-free longitudinal regions.

It was disclosed that the construction of a bone plate actually starts from biomechanical conditions, namely from a favorable bending stiffness and a maximum width. As equations (3), (3a), (3b) and (3c) show, the resistance moments and the moment of inertia are interrelated geometrical magnitudes. An analysis can show how the permissible bending moment depends upon the biomechanical magnitudes S, the width b and the properties of the material. There is a ratio $\sigma_D/E^{\frac{2}{3}}$, which is important for the materials. Numbers are named in the table. It is advantageous when $\sigma_D/E^{\frac{2}{3}}$ amounts to at least 0.06 kp $^{\frac{1}{3}}$/mm$^2$. It is furthermore favorable when the ratios $\sigma_D W/S$, $\sigma_D W_1/S$ and $\sigma_D W_2/S$ are greater than 0.001/mm. These conditions are for example easily fulfilled when the plate 1 is manufactured from the cold-worked stainless steel or cobalt alloy or titanium alloy previously mentioned.

Shown in FIG. 5 is a bone 6, namely a tibia, of a patient. The bone 6 displays two fragments 6a and 6b emanating from a fracture and abutting against each other at the fracture location 7. The two bone fragments 6a and 6b are now connected to each other in an osteosynthesis operation by means of a compression plate 1 and screws 5. The threads of the screws have diameters of at least 3 millimeters approximately and for example 4.5 millimeters. The heads of the screws display approximately hemispherical bearing surfaces. For the fastening of the compression plate, at least one thread is first drilled into the bone fragment 6a and the compression plate 1 is fastened by means of at least one screw 5 in such a manner that its surface 1d rests on the bone 6. Thereafter, the bone fragments 6a and 6b are suitably placed against each other at the fracture location 7. Then, a threaded bore in the bone fragment 6b is produced through the screw hole 1a disposed at the upper end of the plate 1 in the FIG. 5, namely at the end of the slotted screw hole 1a remote from the fracture location 7. Now, one screws a screw 5 into this threaded bore. The formation of the countersink 1b, visible in the FIG. 2, now has the effect that the screw head, on screwing fast, is urged against the end of the screw hole facing the fracture location. The two fragments 6a and 6b are thereby pressed together, while the screw gets approximately into the middle of the screw hole. Now, another threaded bore is drilled into the fragment 6b at the end of another screw hole remote from the fracture location 7 and a screw 5 is inserted. The fragments 6a and 6b are thereby pressed against each other still more firmly. The fragment 6b in that case displaces relatively to the plate 1 towards the fracture location 7 and the screw 5, previously screwed into the fragment 6b, is simultaneously displaced towards the end of the screw hole facing the fracture location 7. The further screws are screwed in as required in a corresponding manner so that the compression plate 1 presses the two fragments 6a and 6b against each other with considerable pressure.

In case a particularly large compressive force has to be exerted on the bone fragments, one can press the bone fragments 6a and 6b against each other already when the plate 1 is first fastened to the fragment 6a. For this purpose, a threaded bore is drilled in the fragment 6b above the upper end, in FIG. 5, of the plate 1 and a plate-tightening device is screwed to the fragment 6b. This displays a hook which can be inserted in the uppermost screw hole and then engages in the groove 1e. The plate-tightening device further displays a threaded spindle to draw the hook and the plate 1 therewith away from the fracture location 7, whereby the two fragments are pressed together. When the plate 1 is prestressed in this manner, it can be fastened also to the fragment 6b by means of a screw 5. The hook of the plate-tightening device can now be unhooked and the plate-tightening device be unscrewed from the bone and removed. The threaded bore drilled in the bone for the screwing-on of the plate-tightening device is then no longer used and can grow closed again. For this, reference is also made to the two initially mentioned books by Müller et al and Allgöwer et al.

The compression plate fastened in one of the previously described ways is of course stressed in tension. When the patient moves and loads the bone 6, there exists additionally a tendency for the plate 1 visible in FIG. 5 to bend along the plane of the drawing, i.e. along the plane indicated earlier by 3. Naturally, considerable bending stresses arise in the plate thereby. The plate is in that case chiefly bent in such a way that tensional stresses appear in the plate region between the neutral surface and the surface 1e which is remote from the bone. Since the plate relative to such bending displays over its entire length an approximately constant resistance moment W as well as approximately constant resistance moments $W_1$ and $W_2$, its bending fracture strength is equally great at the screw holes as between the holes. In this manner, a maximum breaking strength can be obtained without superfluous plate material. The mean bending resistance of the plate 1 stated further above assures that the fracture heals quickly and well, i.e. the fragments 6a and 6b grow together well. Thus, in particular, neither a resorption at the fracture location 7 nor an osteoporosis takes place.

In case the broken bone displays no approximately cylindrical surface in the vicinity of the fracture location, the plate 1 can before the insertion be plastically deformed by the surgeon in known manner by means of forceps or presses in correspondence with the shape of the bone, so that it subsequently bears well against the bone. The bending resistance, approximately constant over the entire length of the plate, in that case assures particularly that during the plastic deforming and, in particular, the bending of the plate, kinks result nowhere, but a regular curvature results everywhere. This adaptation is an important part of the operational technique.

The plate 11 illustrated in FIGS. 6 and 7 is likewise intended for the osteosynthesis of the tibia and the upper arm bone and displays screw holes 11a with countersinks 11b. However, in contrast to the screw holes 1a of the plate 1, the screw holes 11 are rotationally symmetrical, i.e. are formed by drillings. For the remainder, the plate 11 is constructed similarly as the plate 1. It displays grooves 11c particularly at the ends of the plate 1. The surface 11d, intended to rest on the bone, is concave and cylindrical over its entire length. The surface 11e lying opposite it is convexly curved and has convex bulges in the longitudinal sections containing the countersinks 11b. The two other longitudinal surfaces 11f are outwardly bowed in the regions of the screw holes. The cross-sectional dimensions and shapes vary along the plate 11 in such a manner that the bending resistance moments W, $W_1$, $W_2$ remain constant over the entire length of the plate within the tolerance limits indicated for the plate 1. The mean bending stiffness likewise lies within the range of values indicated for the plate 1.

Since the screw holes 11a are not slot-shaped, but formed by drillings, the plate, on being screwed fast to a bone, is not shifted with respect thereto. The plate 11 is therefore suitable for a technique, in which the repositioning and compression is attained by other means, e.g. a spanner. A given compressive force then lets itself be attained, in that the plate 11 is first screwed to only one bone fragment and then tightened by means of a plate-tightening device fastened to the other fragment, as has already been described for the plate 1.

Figure 8:
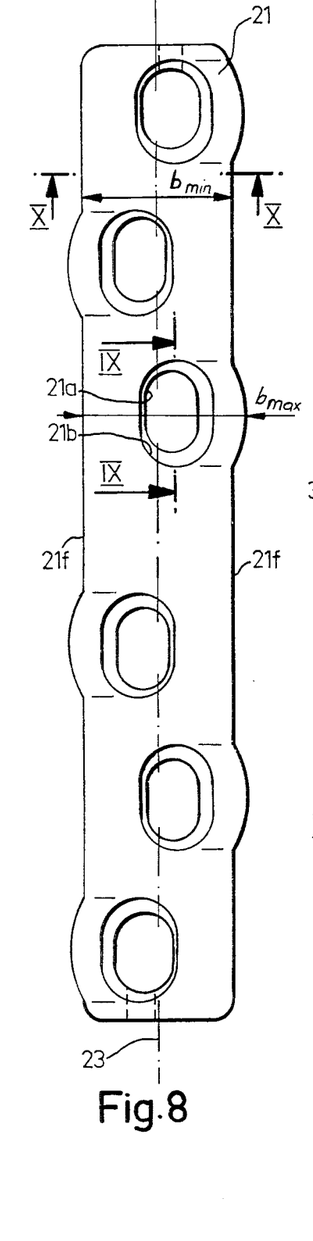
FIG. 8 shows a plan view of a plate embodying the invention for femur fractures.
Figures 9, 10:
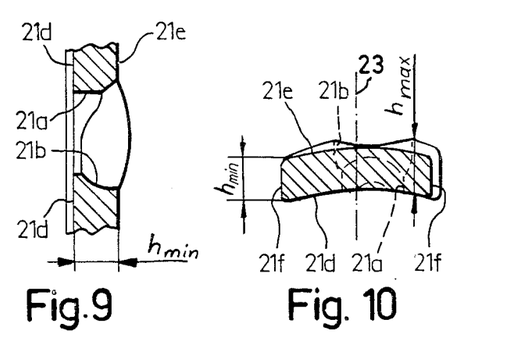
FIG. 9 shows a section along the line IX—IX of the FIG. 8.
FIG. 10 shows a section along the line X—X of the FIG. 8.

The compression plate 21 illustrated in FIGS. 8, 9 and 10 displays six slot-shaped screw holes 21a with countersinks 21b and mutually parallel passage directions. The screw holes 21 display shapes similar to the screw holes 1a of plate 1. However, they are asymmetrical in cross-section (FIG. 10) and laterally displaced towards the longitudinal center plane 23 of the plate 21 parallel to their passage directions. As is evident from FIG. 8, successive screw holes 21a are displaced towards opposite sides. The screw holes 21a display clear widths measured across the longitudinal direction of the plate of at least 5 millimeters, namely the four inner screw holes a width of 5.5 millimeters and the two outermost a width of 6.5 millimeters. The surface 21d intended to rest on a bone is cylindrical over the entire length of the plate and concavely curved in cross-section. The surface 21e opposite it is cylindrical in the longitudinal regions between the screw holes, namely convex as well as about co-axial to the surface 21d. In the longitudinal sections containing the screw holes, the surface 21e is bulged out. Its bulges are however not symmetrical in cross-section as for the plates 1 and 11, but asymmetrical. As is evident from FIG. 10, the surface 21e is more markedly bulged on that side of the plate 21 on which the screw hole concerned is disposed. The narrower mutually opposite longitudinal surfaces 21f are parallel to the passage direction of the screw holes 21a and to each other in the hole-free longitudinal sections. In the longitudinal sections containing the screw holes, that respective surface 21f is outwardly bulged which is disposed nearer the screw hole concerned.

The larger compression plate 21 is intended for the treatment of fractures of the femur (thigh bone). Its width b has, in the longitudinal sections between the screw holes, a minimum value $b_{min}$ of 15 to 18 millimeters, for example about 16 millimeters. Its height h measured perpendicularly to the surface intended to rest on the bone, has in the longitudinal regions between the screw holes a minimum value $h_{min}$ of 4 to 5.5 millimeters, for example 4.5 millimeters. In the longitudinal sections containing the screw holes 21a, the width and height are again increased in such a manner that the bending resistance moments W, $W_1$ and $W_2$ within the limits stated for the plate 1 are equally great at the screw holes as in the hole-free intermediate regions. In that case, the resistance moments again are meant in respect of a bending in which the plate 21 is bent along the longitudinal center plate 23, which runs through the center lines of the hole-free longitudinal sections, cuts the surface 21d at right angles and thus also runs parallel to the passage direction of the screw holes. The maximum value $b_{max}$ of the width b at the screw holes is at a maximum about 5 to 10% greater for example than the width $b_{min}$ in the regions between the screw holes. The height h is there, where it has its maximum $h_{max}$ at the screw holes, 25 to 40%, for example about 35%, greater than in the longitudinal regions between the screw holes, where it has the value $h_{min}$.

Since the plate 21 is intended for the treatment of femur fractures, its resistance moment and its mean bending resistance shall be greater than for the plates 1 and 11. The plate 21 shall therefore display a bending resistance moment of at least 40 mm$^3$, perhaps 50 mm$^3$, and a mean bending stiffness S of $8 \cdot 10^5$ to $30 \cdot 10^5$ kp mm$^2$. The plate 21 can be produced of the same materials as the plate 1. The ratio of fatigue strength with repeated bending stress $\sigma_D$ to modulus of elasticity E shall, as for the already discussed plates, be as great as possible and the ratio $\sigma_D/E^{\frac{3}{2}}$ shall preferably display the minimum value recommended for the plate 1. The previously stated bending stiffness applies to the treatment of fractures of the middle part of the femur. For treatment in the region of the trochanter and condyle, i.e. the thickenings at the upper and lower end of the femur, still somewhat stronger plates with an average bending stiffness of $40 \cdot 10^5$ to $70 \cdot 10^5$ kp mm$^2$ are expediently used. These plates can display the same width and arrangement of screw holes as the plate 21, but a somewhat greater height. In that case, the bending resistance moment can again be made nearly constant over the entire length of the plate. The femur plates and plates for the condyle and trochanter can thus display a width $b_{min}$ of 15 to 18 millimeters and a mean bending stiffness S of $8 \cdot 10^5$ to $70 \cdot 10^5$ kp mm$^2$ in the region between the screw holes.

Figure 11:
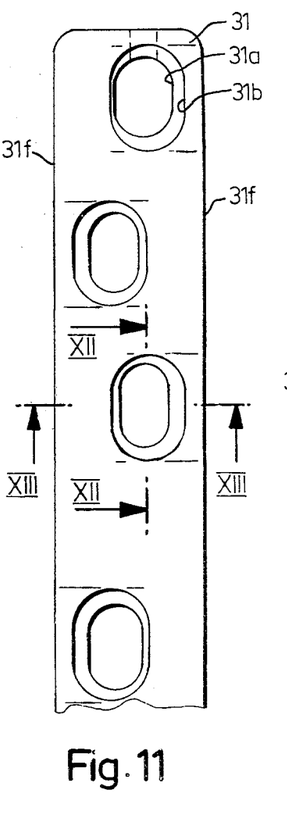
FIG. 11 shows a plan view of a plate embodying the invention for a femur, in which only the height is greater at the screw holes.
Figure 12:
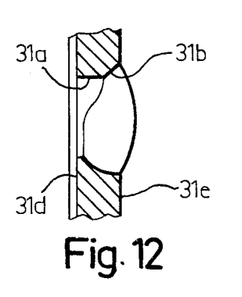
FIG. 12 shows a section along the line XII—XII of the FIG. 11.
Figure 13:
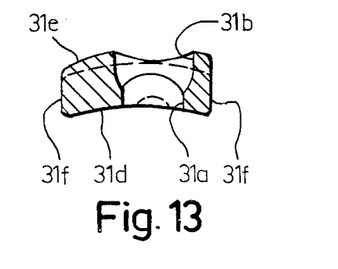
FIG. 13 shows a section along the line XIII—XIII of the FIG. 11.

The compression plate 31 illustrated in FIGS. 11, 12 and 13 is likewise intended for the treatment of femur fractures and displays slot-shaped screw holes 31a with countersinks 31b. Its surface 31d intended to rest on the bone is concavely curved and cylindrical over its entire length. The surface 31e opposite it displays outward bulges at the screw holes. The two narrower mutually opposite longitudinal surfaces 31f are, in contrast to the corresponding surfaces of the previously described plates 1, 11 and 21, parallel to each other over their entire length. Thus, in the plate 31, only the height h, but not the width b, is greater at the screw holes than in the longitudinal sections between the screw holes. In the hole-free regions, the plate 31 is developed and dimensioned similarly to the plate 21 and also the screw holes are about identical in the two plates. Since the bending resistance moments W, $W_1$ and $W_2$ shall again be at least nearly constant over the entire length of the plate, the surface 31e must be somewhat convexly bulged somewhat more markedly at the screw holes than the surface 21e of the plate 21. The maximum height at the screw holes is, according to their dimensions and the cross-sectional shape of the convex bulges, about 30 to 50%, for example 40%, greater than in the hole-free longitudinal sections of the plate.

In use, the compression plates 21 and 31 can be fixed to a femur in a manner analogous to that in which the plate 1 is fastened to a tibia.

A few variants shall now be mentioned. The plates can of course display, instead of six screw holes, also another number of screw holes. Furthermore, the plates can also display other outline shapes in cross-section. The cross-section could for example be rectangular. Furthermore, the plates provided for the treatment of femur-fractures and displaying a width of 15 to 18 millimeters in the hole-free regions could be provided with bores instead of slot-shaped screw holes. For the rest, it would be possible in the case of the femur plates to make the height h constant over the entire length of the plate and to increase only the width at the screw holes in such a manner that the bending resistance moments remain approximately constant over the entire length of the plate.

It is also possible in the case of the plates intended for tibia fractures and displaying a width of 10 to 14 millimeters in the hole-free regions, to vary only the height or only the width along the longitudinal direction of the plate. However, in these small plates, the area of the screw holes is relatively large in comparison with the cross-sectional area of the plate material. When therefore only the height or only the width is varied to attain a constant resistance moment over the entire plate length, relatively large curvatures of the surfaces concerned are necessary. This is particularly the case when only the width is varied. Since pronounced projections are to be avoided as far as possible because of the risk of injury to the surrounding tissue, it is therefore advantageous in the case of the small plates not to increase exclusively only the width at the screw holes, but the width as well as the height or in all cases only the height.

Numerical values shall now be given for some of the magnitudes of the plates and will be compared with the corresponding magnitudes of known plates, displaying constant cross-sectional dimensions over their entire length.

A known plate envisaged for the treatment of tibia fractures, may over its entire length have a constant width of 12 millimeters and a height of 4 millimeters. When the screw holes of this plate correspond in shape and dimensions to the screw holes $1a$ of the plate 1, then the bending resistance moment W, that at most places is equal to moments $W_1$ and $W_2$, has a maximum value of 28 mm$^3$ in the longitudinal sections possessing a complete cross-section, i.e. those disposed between the screw holes, and a minimum value of about 11 mm$^3$ in the regions of the screw holes, the values being calculated numerically. The mean polar moment of inertia amounts to about 45 mm$^4$. A plate, which is developed somewhat in accordance with FIGS. 1 to 3 and has a width of 12 millimeters and a height of 3.5 millimeters in the regions between the screw holes, has likewise a mean polar moment of inertia of 45 mm$^4$ approximately. The resistance moment of this plate however amounts to about 23 mm$^3$ over the entire length. The plate thus has a bending resistance moment W in the region of the screw holes, that is approximately twice as great as that of the plate formed by a profile rod. This increase of the resistance moment W and also the approximately equal increase of the moments $W_1$ and $W_2$ results for the same plate material in a corresponding increase of the maximum permissible bending moment with a continually alternating loading, as could be confirmed by reference to bending-fatigue experiments. The local strengthening of the plate at the screw holes, in accordance with the invention, thus enables the repeated bending load-capacity to be doubled, without the biomechanically important mean bending resistance thereby becoming greater.

The plates illustrated in FIGS. 1 to 13 also still have the advantage that they are plastically deformable without difficulty in the adaption to the shape of the bone in such a manner that kinks arise nowhere, but only steady curves.

The plates illustrated in FIGS. 1 to 13, for which the height is greater in the region of the screw holes than between these, have a greater bending stiffness in the region of the screw holes than between these. Therefore, also only minimal relative movements occur between the plate and the screws on changes of the loading. Correspondingly, the fretting corrosion and the abrasion of the material of the plates and screws is also only small and, in particular smaller than in plates, not in accordance with the invention and formed by profile rods. This is of advantage, because the particles rubbed off can trigger chemical reactions and damage the surrounding body tissue.

In the following table, the mean bending stiffnesses as well as the maximum bending moments with repeatedly changing load are given for three different applications for plates made of stainless steel or titanium. The bending moments in that case are given for the case of plates, not in accordance with the invention and with constant width b and height h, and for plates, in accordance with the invention, the height and width of which is increased in the region of the screw holes in such a manner that the bending resistance moments W, $W_1$ and $W_2$ are approximately constant. In the table, in accordance with the already used designations, $b_{min}$ designates the width of the plate between the holes, S the mean bending stiffness and $M_{max}$ the maximum permissible bending moment.

| Application | $b_{min}$ (mm) | S (kp mm$^2$) | $M_{max}$ plate with b, h constant (kp mm) | $M_{max}$ plate with W constant (kp mm) |
| --- | --- | --- | --- | --- |
| Tibia | 10–14 | 3–7.10$^5$ | 200–400 | 500–1100 |
| Femur | 15–18 | 8–30.10$^5$ | 800–1200 | 1400–2200 |
| Trochanter, Condyle | 15–18 | 40–70.10$^5$ | 1600–2400 | 2500–3500 |

The comparison of the last two columns of the table shows that the maximum permissible bending moment for the plates with constant bending resistance moments is in all cases at least 50% greater than for the plates of constant width and height. For the rest, the width and height variations can be so fixed in the plates in accordance with the invention that for a smallest possible plate volume there results, for given mean bending stiffness, the bending resistance moments being approximately constant and as great as possible over the entire length of the plate.

I claim:

1. An elongate plate for osteosynthesis, comprising at least two means each defining a respective hole for receiving a screw, and a respective hole-free section extending in the longitudinal direction of the plate and separating each neighboring pair of the means defining the holes, a spacing, perpendicular to the longitudinal direction of the plate, between the same two mutually opposite surfaces of at least two of said hole-defining means being greater than that between two mutually opposite surfaces of the hole-free sections, the plate exhibiting at least in the region of the at least two hole-defining means a bending resistance moment $W=I/e$ along a plane extending substantially centrally of the plate in the longitudinal direction of the plate and intersecting substantially perpendicularly that surface of the plate which is intended to rest on a bone, the bending resistance moment $W=I/e$ lying between a lower and an upper limiting value, the lower limiting value being at most 30% smaller than the upper limiting value, wherein I is the area moment of inertia, and e is the maximum value of the distance of the outline bounding the cross-sectional area from a neutral surface of the plate.

2. A plate as claimed in claim 1, wherein the plate height, measured perpendicularly to the longitudinal direction and parallel to said plane, is greater at each of the hole-defining means than at each of the hole-free sections.

3. A plate as claimed in claim 1, wherein the plate height, measured perpendicularly to the longitudinal direction and parallel to said plane, is greater at each of the hole-defining means than at each of the hole-free sections, and wherein the plate width, measured perpendicularly to the plane, is greater in the region of each of the hole-defining means than at each of the hole-free sections.

4. A plate as claimed in claim 3, wherein the plate width is at most 20% greater in the region of the hole-defining means than at the hole-free sections.

5. A plate as claimed in claim 1, wherein the lower limiting value of the bending resistance moment W is at most 15% smaller than the upper limiting value.

6. A plate as claimed in claim 1, wherein the mean bending stiffness of the plate lies between $3 \cdot 10^5$ and $7 \cdot 10^5$ kp mm$^2$ when the plate width measured at right angles to the longitudinal central plane is between 10 and 14 millimeters in the region between the hole-defining means, the mean bending stiffness being equal to the mean value of the product of the modulus of elasticity times the area moment of inertia.

7. A plate as claimed in claim 1, wherein the mean bonding stiffness of the plate lies between $8 \cdot 10^5$ and $70 \cdot 10^5$ kp mm$^2$ when the plate width measured at right angles to the longitudinal central plane is between 15 to 18 millimeters in the region between the sections containing the holes, the mean bending stiffness being equal to the mean value of the product of modulus of elasticity times the area moment of inertia.

8. A plate as claimed in claim 1 and comprising cold-worked stainless steel containing 17 to 20% chromium, 10 to 15% nickel, and 2 to 4% molybdenum, balance substantially all iron.

9. A plate as claimed in claim 1 and comprising a metal with at least 75% titanium.

10. A plate as claimed in claim 1 and comprising a wrought cobalt alloy with 20 to 70% cobalt.

11. A plate as claimed in claim 1 and comprising a metal, for which the magnitude $\sigma_D/E^{\frac{2}{3}}$ amounts to at least 0.06 kp$^{\frac{1}{3}}$ mm$^{\frac{2}{3}}$, wherein $\sigma_D$ is the fatigue strength with repeated bending stress and E is the modulus of elasticity.

12. A plate as claimed in claim 1, wherein the plate cross-sectional dimensions vary over the plate length in such a manner that the ratio of the resistance moment W and the mean area moment of inertia $\bar{I}$ amounts to at least 0.3/mm.

13. A plate as claimed in claim 1, wherein the plate cross-sectional dimensions are matched to the plate material in such a manner that $\sigma_D W/S$ is greater than 0.001 mm$^{-1}$, wherein $\sigma_D$ is the fatigue strength with repeated bending stress and S is the mean bending stiffness which is equal to the mean value of the product of the modulus of elasticity times the area moment of inertia.

14. A plate as claimed in claim 1, wherein the bending resistance moment $W_1 = I/e_1$, lies between two limiting values, of which the lower limiting value is at most 30% smaller than the higher limiting value, $e_1$, being the maximum value of the distance of the outline bounding the cross-sectional area from the neutral surface on the side remote from the bone.

15. A plate as claimed in claim 14, wherein the lower limiting value of the bending resistance moment $W_1$ is at most 15% smaller than the upper limiting value.

* * * * *